United States Patent
Hartlaub et al.

(10) Patent No.: US 6,282,450 B1
(45) Date of Patent: Aug. 28, 2001

(54) SYSTEM AND METHOD FOR STORING FIRMWARE IN A HUMAN-IMPLANTABLE MEDICAL TREATMENT DEVICE

(75) Inventors: Jerome T. Hartlaub, New Brighton; Earle T. Roberts; David C. Ullestad, both of Maple Grove, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/303,032

(22) Filed: Apr. 30, 1999

(51) Int. Cl.[7] ....................................... A61N 1/08
(52) U.S. Cl. ............................................... 607/59
(58) Field of Search .................. 607/59, 60, 30, 607/32

(56) References Cited

U.S. PATENT DOCUMENTS

| | | | |
|---|---|---|---|
| 5,318,593 | * 6/1994 | Duggan | 607/9 |
| 5,360,437 | 11/1994 | Thompson | 607/30 |
| 5,456,691 | 10/1995 | Snell | 607/30 |
| 5,456,692 | 10/1995 | Smith et al. | 607/31 |
| 5,653,735 | * 8/1997 | Chen et al. | 607/9 |
| 5,713,922 | 2/1998 | King | 607/2 |
| 5,782,798 | 7/1998 | Rise | 604/49 |
| 5,814,014 | 9/1998 | Elsberry et al. | 604/43 |

* cited by examiner

Primary Examiner—Jeffrey R. Jastrzab
(74) Attorney, Agent, or Firm—Banner & Witcoff, Ltd.

(57) ABSTRACT

In a medical treatment device implanted within the body of a patient, a system and method for organizing storage of the device's firmware in ROM, RAM, and EEPROM such that a ROM-based system is implemented initially using pointers stored in RAM, which RAM-based pointers point to ROM-based functions. When revisions to the functionality of the treatment device are desired, code is downlinked via an external programmer and telemetry to link to RAM, and one or more pointers, as appropriate, which pointers point to the downlinked code in RAM, are downlinked to RAM. In this manner, revisions to the firmware of an implanted medical treatment device can be downlinked to the device thereby eliminating the need to explant the device in certain circumstances. The amount of code placed in ROM is maximized, with only pointers to functions and new or revised code segments stored in RAM as needed.

15 Claims, 4 Drawing Sheets

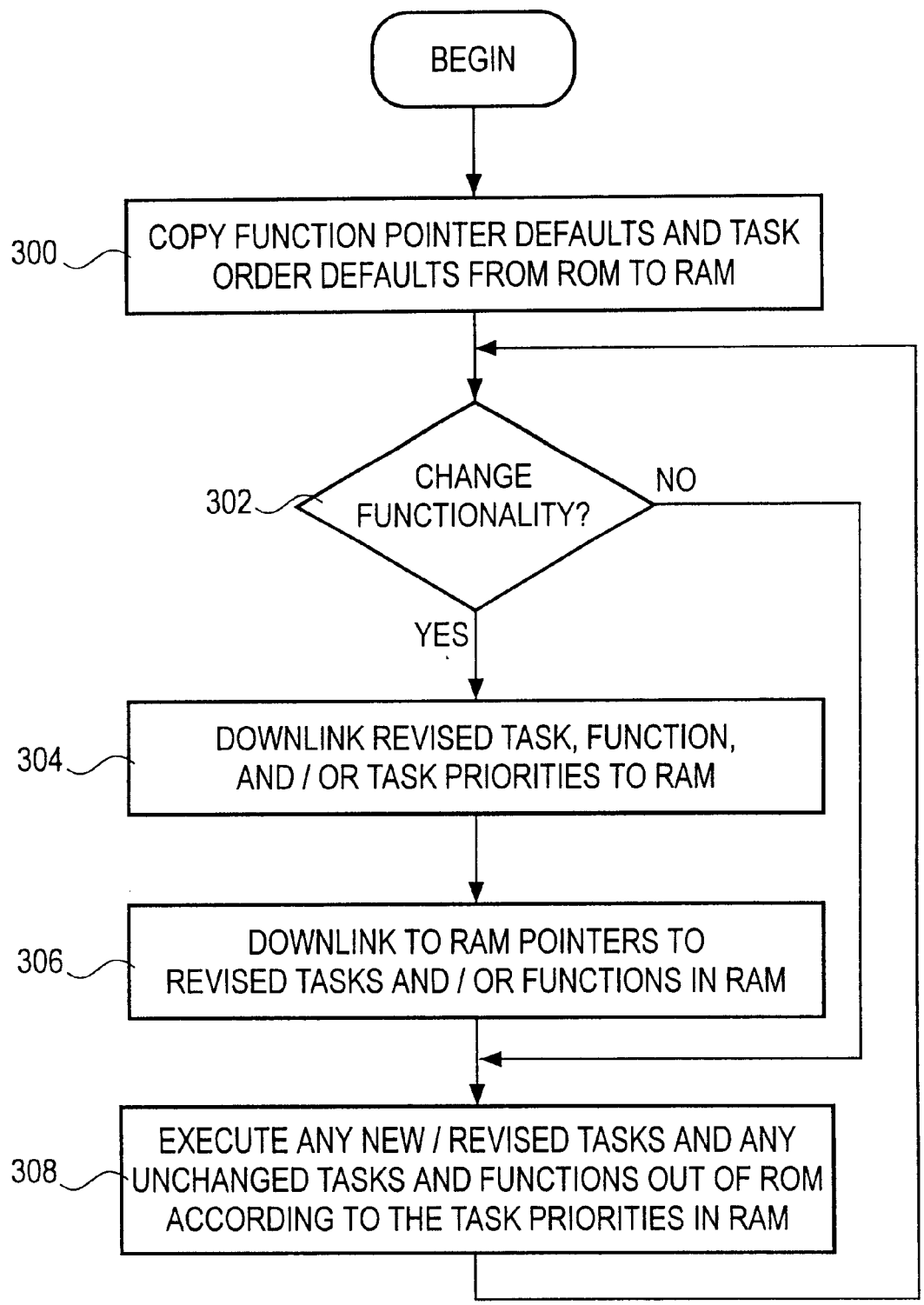

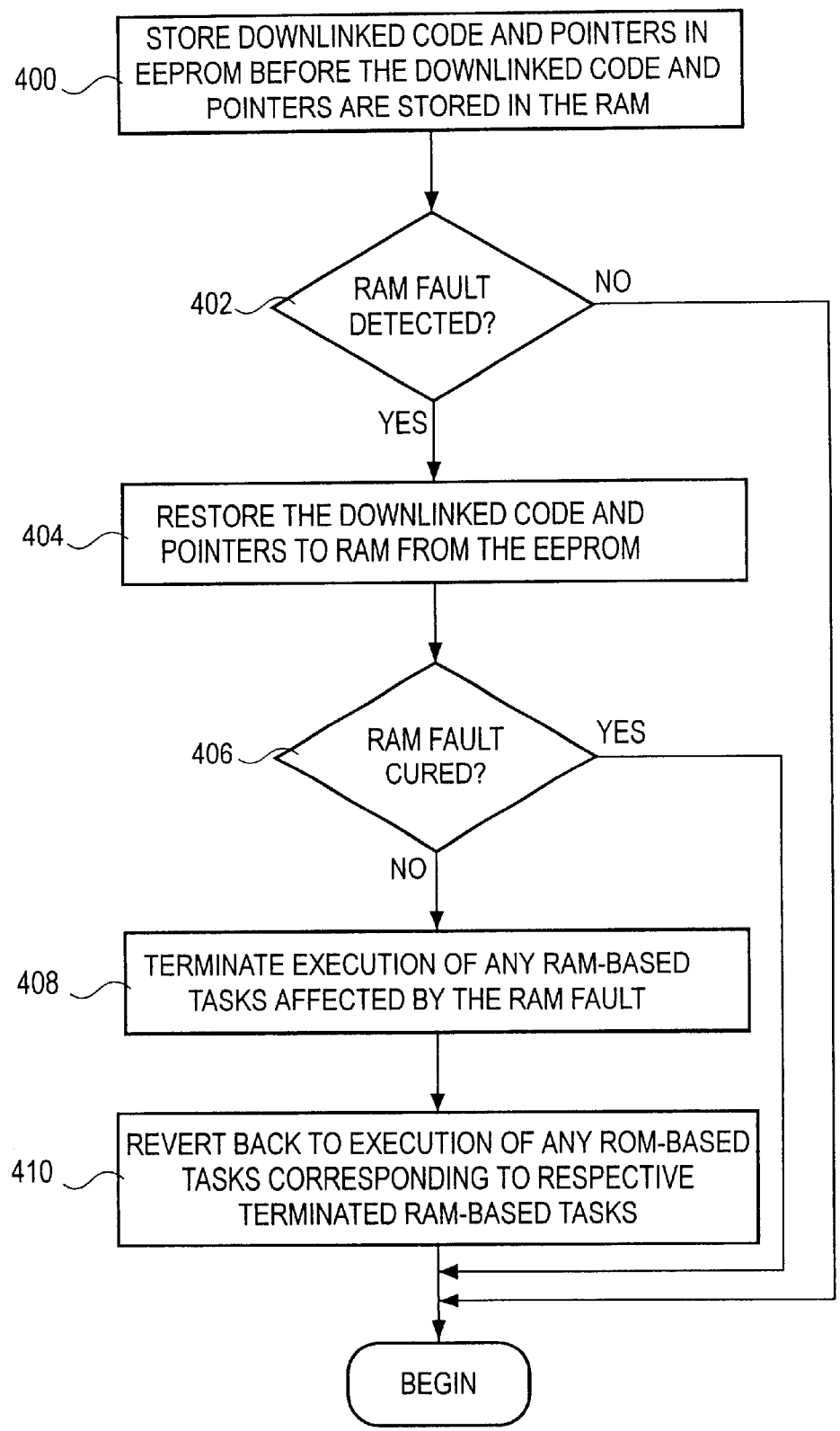

SYSTEM AND METHOD FOR STORING FIRMWARE IN A HUMAN-IMPLANTABLE MEDICAL TREATMENT DEVICE

BACKGROUND OF THE INVENTION

1. Field of the Invention

This invention relates to storing firmware in a medical treatment device, such as a drug infusion pump or an electrical nerve stimulator, that is implanted within a patient's body and downloading revisions and/or additions to the firmware without explanting the treatment device.

2. Background of the Invention

Devices and techniques for treating neurological disorders by drug infusion and by electrical stimulation of a person's central nervous system are well known in the prior art. For instance, U.S. Pat. No. 5,713,922 to King, U.S. Pat. No. 5,782,798 to Rise, and U.S. Pat. No. 5,814,014 to Elsberry et al., each assigned to Medtronic, Inc. of Minneapolis, Minnesota, disclose such devices and techniques and are incorporated herein by reference.

Such treatment devices and techniques often employ drug-infusion pumps and/or electrical pulse generators that are implanted within a patient's body. Accordingly, available memory for storing control software and operating parameters, also referred to as firmware, such as treatment dose, duration, and timing, of various treatment protocols is severely limited relative to the amount of memory typically available to systems that are not implanted within a person's body.

The of use random access memory ("RAM") and read only memory ("ROM") each have their advantages and disadvantages in the context of implantable medical treatment devices. With respect to accessing memory, ROM uses less energy and is therefore preferable to RAM for storing the firmware of an implantable medical treatment device because it increases the useful life of the device, thereby reducing the need for explanting a device due to a discharged battery. ROM, however, is less flexible to the extent that RAM can be modified, whereas ROM can not be modified without explanting the device. The flexibility provided by the capability to modify RAM also raises concerns about RAM-based code becoming unintentionally corrupted. ROM storage devices offer another advantage, namely, ROM devices typically require less area on an integrated circuit chip thereby advantageously reducing the size of the treatment device.

Making modifications to the software for controlling such treatment devices without explanting the devices is often desirable. For instance, modifications to the control software are desirable as new treatment modes are developed.

Optimization techniques for efficiently using the limited amount of available memory provided by an implantable treatment device have been addressed by certain prior art patents. For instance, U.S. Pat. No. 5,360,437 to Thompson discloses an implantable medical device having its control program or software stored in non-volatile random access memory ("RAM"). The non-volatile RAM can be re-programmed as desired using an external programmer and a telemetry link. U.S. pat. No. 5,456,691 to Snell discloses a system in which only certain physician-selected program modules are loaded into the implantable device's RAM. RAM requirements can be reduced by loading only a limited number of program modules into RAM. These approaches undesirably fail to take advantage of the benefits provided by maximizing the use of RAM.

U.S. Pat. No. 5,456,692 to Smith, Jr. et al. discloses an implantable pacemaker in which the control program is stored in read only memory ("ROM") or an equivalent non-volatile memory storage device. Control parameters, on the other hand, are stored in RAM, and may be programmably altered in order to allow the pacemaker to meet the potentially changing needs of a patient. A drawback to this approach, however, is that it is difficult to predict all of the parameters that may need to be modified in the future. For instance, the motor of an implantable drug-infusion pump is typically powered by a battery that outputs electrical pulses of varying characteristics as the battery voltage decreases. For instance, a filly charged battery could drive the pulses at a 10% duty cycle, while a substantially discharged battery's duty cycle could expand to close to 100%. If the developers of the control software for a drug infusion pump were unaware that changing the battery duty cycle characteristics would be desirable or necessary in the future, the related parameters would likely not be placed in RAM. If those parameters were placed in ROM, they could not be changed without explanting the pump.

Accordingly, in light of the significant memory power and size limitations and the safety concerns associated with storing control or operating software in an implantable medical device, there remains a need for an improved system and method providing a flexible arrangement that takes advantages of the benefits provided by the use of both ROM and RAM in the context of an implantable medical treatment device.

SUMMARY OF THE INVENTION

In a first embodiment of this invention, a system for storing control software in a human-implantable medical treatment device is provided including a read only memory ("ROM"), a random access memory ("RAM"), and an external programmer and telemetry link for downlinking code to the RAM, which downlinked code is capable of causing the implanted medical treatment device to perform new and/or revised functionality. The firmware, also referred to as control software, is stored in such a manner that the amount of code stored in ROM is maximized and RAM storage is used for storing pointers to functions, the relative priority and/or execution order of functions, and any code downlinked via the external programmer and telemetry link. When code is downlinked to and stored in RAM, one or more revised and/or new pointers to the code that has been downlinked to RAM are also downlinked and stored in RAM. In this manner, execution of ROM-based tasks can be terminated by downlinking a pointer to execute a downlinked task in RAM, instead of executing a ROM-based task.

In another embodiment of the present invention, the ROM stores a task scheduler and the code of a plurality of tasks to be performed by the medical treatment device. The RAM stores pointers to the ROM-based tasks. The programmer and telemetry link download, to the RAM, code and pointers to the downlinked code so that the medical treatment device then executes both ROM-based tasks and downlinked RAM-based tasks. The downlinked code and pointers may be stored in an electrically erasable programmable read only memory ("EEPROM") before the downlinked code and pointers are stored in the RAM. Upon detecting a RAM fault, the RAM-based downlinked code and pointers may be restored from the contents of the EEPROM. Upon failure of the restoration of RAM from EEPROM, execution of one or more RAM-based functions may be terminated, and execution of one or more ROM-based tasks can be reinstated.

The ROM may contain a function defaults module for storing functions in the ROM, a function pointer defaults module for storing pointers to the functions stored in the function defaults module of the ROM, an executive/task scheduler for executing functions pointed to by stored function pointers, and a task order defaults module for defining the initial order in which ROM-based tasks are executed based, at least in part, upon the order in which pointers to tasks are stored in the task order defaults module.

The RAM may contain a function pointer table initialized by copying the contents of the function pointer defaults module from the ROM and for storing pointers to the functions executed by the executive/task scheduler, a downlinked functions module for storing downlinked functions in addition to the functions stored in the function defaults module of the ROM, and a task order table initialized by copying the contents of the task order defaults module of the ROM and for storing downlinked definitions of the order in which ROM-based tasks or RAM-based tasks, or both ROM-based tasks and RAM-based tasks, are executed.

The EEPROM may contain a function pointer changes module for storing a back-up copy of the contents of the function table pointer of the RAM, a function changes module for storing a back-up copy of the downlinked functions module of the RAM, and a task order changes module for storing a back-up copy of the task order table of the RAM.

In yet another embodiment of this invention, a method of storing control software in a human-implantable medical treatment device is provided, which includes the steps of storing a task scheduler and the code of a plurality of tasks to be performed by the medical treatment device in a ROM, storing pointers to the tasks in a RAM, and downlinking to the RAM code and pointers to the downlinked code such that the medical treatment device executes both the ROM-based tasks and the RAM-based downlinked tasks. Steps for implementing a tiered fault recovery strategy analogous to the one set forth above with respect to the first embodiment may also be included.

BRIEF DESCRIPTION OF THE DRAWINGS

FIG. 3 is a simplified flow chart depicting steps for storing the firmware of an implantable medical treatment device in accordance with the principles of this invention.

FIG. 4 is a simplified flow chart depicting steps for implementing a tiered fault recovery strategy in accordance with the principles of this invention.

DETAILED DESCRIPTION OF THE PREFERRED EMBODIMENTS

Figure 1:
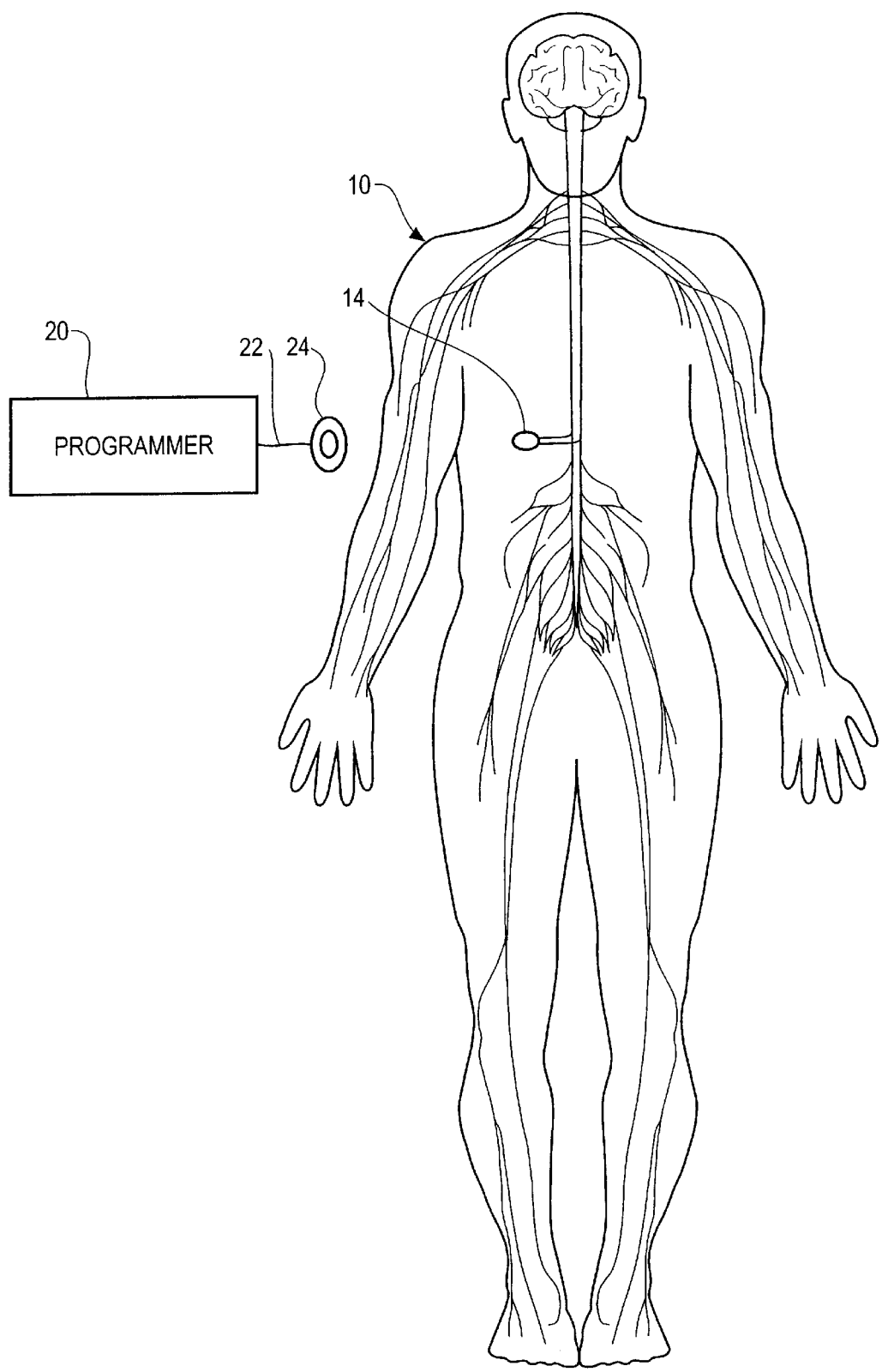
FIG. 1 is a schematic view of a patient with a treatment device implanted within the patient's body.

FIG. 1 is a schematic view of a patient 10 having treatment device 14 implanted within the patient's body. Implantable treatment device 14 is programmable through a telemetry link from programmer 20, which is coupled via a conductor 22 to a radio frequency antenna 24.

Figure 2:
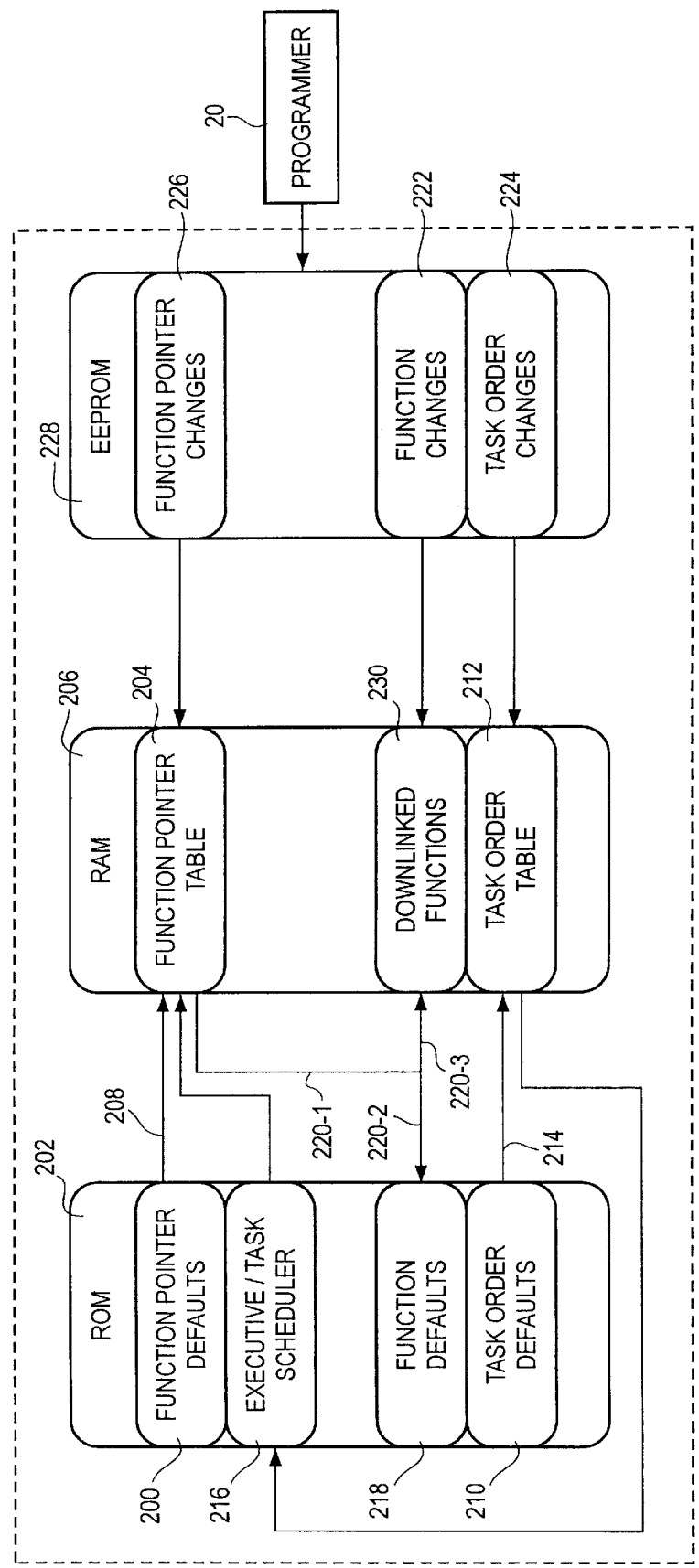
FIG. 2 is a data flow diagram showing the flow of data between portions of different types of memory storage devices in accordance with the principles of this invention.

FIG. 2 is a data flow diagram showing the flow of data between portions of different types of memory storage devices within treatment device 14 in accordance with the principles of this invention. Upon initialization of the implanted medical device 14, function pointer defaults 200 are copied from read only memory ("ROM") 202 into function pointer table 204 in random access memory ("RAM") 206, as indicated by arrow 208. RAM 206 could be an FRAM as disclosed in commonly assigned U.S. Pat. No. 5,360,437 to Thompson, which is incorporated herein by reference. Of course other suitable storage devices could also be used.

Also during initialization of device 14, task order defaults 210 are copied into task order table 212, as indicated by arrow 214. This task order data specifies relative priorities among tasks to be executed. Upon completion of initialization, executive/task scheduler 216 executes tasks in the order in which they appear in task order table 212. Functions, methods, subroutines, and the like, that are part of one or more tasks, are called using pointers to functions, which pointers are contained in function pointer table 204.

Tasks generally refer to higher level routines, whereas functions generally refer to lower-level routines, as these terms are used in this specification. There is no bright-line distinction, however, between the way the terms task and function are used herein. Accordingly, the terms should be considered interchangeable for purposes of this specification, including the appended claims. The term code as used herein includes, but is not limited to, program instructions, variables, constants, pointers, and the like.

Under normal operation, upon completion of initialization, function pointer table 204 contains pointers to functions contained in function defaults 218 within ROM 202. These pointers are symbolically represented in FIG. 2 as two-segment arrow 220-1 and 220-2. Accordingly, the ROM-based software for implementing the original functionality of device 14 is stored in executive/task scheduler 216 and function defaults 218 of ROM 202.

When a modification, addition to, or deletion from, the control software of device 14 is desired, software for implementing revised functionality or new functionality is downlinked from programmer 20 and stored in function changes module 222. One or more corresponding revised function pointers are downnliked from programmer 20 to function pointer changes module 226. The revised function pointers are then copied from the function pointer changes module 226 of EEPROM module 228 to function pointer table 204. The revised function pointers point to downlinked functions module 230 in RAM 206, as depicted by double segment arrow 220-1 and 220-3. Downlinked functions module 230 then contains a copied version of the contents of function changes module 222.

Revisions to the priority or order in which tasks are executed can be downlinked to task order changes module 224 and then copied into task order table 212. In this manner, new tasks can be added, existing tasks can be deleted, and tasks can be prioritized relative to one another. Because every major task is called based on a pointer to a function, at any level in the control program, whether it's at a task level or a function level, a revised or new task or function can be downlinked and replace an existing task or function by also changing the corresponding task or function pointer to no longer call the original ROM-based function and to call the downlinked, revised or new, RAM-based task or function instead.

Although task scheduler 216 is depicted separately from other functions, it may be modified by downlinking code to RAM 206 to modify the functionality of task scheduler 216 in an analogous manner as set forth for other functions.

While no foreground tasks are executing, CRC checks are typically run in the background on ROM 202, RAM 206, and EEPROM 228. By having back-up copies of the RAM-based downlinked functions module 230 and task order table 212 in function changes 222 and task order changes 224 in EEPROM 228, if any errors are detected in either downlinked functions module 230 or task order table 212, the errors can be corrected by copying the corresponding back-up version of the data from EEPROM 228.

If a latent failure occurs in a particular area of ROM or RAM, any tasks and/or functions located in the affected area of ROM or RAM may become inoperable. In accordance with the principles of this invention, firmware may be downlinked to RAM, along with one or more corresponding revised function pointers, so that replacement functions for the inoperable tasks and/or functions can be operated out of RAM, instead of ROM. As a result, the need to explant the implanted medical device as a result of certain latent memory failures can be avoided. Details of a tiered fault recovery strategy for recovering from a RAM fault are set forth below in the discussion of FIG. 4.

FIG. 3 is a simplified flow chart depicting steps for executing tasks and/or functions out of ROM 202 and/or RAM 206, as desired, in accordance with the principles of this invention. Initially, as depicted at 300, function pointer defaults and task order defaults are copied from ROM 202 to RAM 206. Whether a change in the functionality of the implanted medical treatment device is desired is checked as depicted at 302. If such a change in functionality is desired, revised task, function, and/or task priorities are downlinked to RAM 206, as depicted at 304. Then, as depicted at 306, pointers are downlinked to RAM 206, which pointers point to the revised one or more tasks and/or functions downlinked to RAM 206 in step 304. Then, existing ROM-based tasks and functions for which no modification has been downlinked in steps 304 and 306 are executed from ROM in the normal fashion and any downlinked tasks or functions are executed from RAM, as depicted at 308. Processing then returns to step 302 to check whether additional functionality changes are desired. If so, steps 304 and 306 are repeated. If no additional functionality changes are desired, steps 304 and 306 are bypassed and processing proceeds to step 308.

Referring to FIG. 4, downlinked code and pointers are stored in EEPROM 228 before they are stored in RAM 206, as depicted at 400. If a RAM fault is detected, the RAM-based downlinked code and pointers are restored from EEPROM, as depicted at 402 and 404. If restoring the downlinked code and pointers from EEPROM does not cure the RAM fault, execution of any RAM-based tasks affected by the RAM fault is terminated, as depicted at 406 and 408, and execution of any ROM-based tasks corresponding to respective terminated RAM-based tasks is reinstated as depicted at 410.

This invention has been described with reference to certain preferred embodiments. Modifications may occur to others upon reading and understanding the foregoing detailed description. This invention includes all such modifications to the extent that they come within the scope of the appended claims or their equivalents.

We claim:

1. A system for storing control software in a human-implantable medical treatment device, the system comprising:
   a read only memory ("ROM") storing a plurality of ROM-based tasks to be performed by the medical treatment device;
   a random access memory ("RAM") storing a plurality of respective ROM-based task pointers pointing to the ROM-based tasks;
   a programmer and telemetry link for downlinking to the RAM
   at least one RAM-based task thereby producing at least one downlinked RAM-based task,
   at least one RAM-based task pointer thereby producing at least one downlinked RAM-based task point, so that the medical treatment device uses at least one of the ROM-based task pointers to execute at least one of the ROM-based tasks and uses at least one of the downlinked RAM-based task pointers to execute at least one of the downlinked RAM-based tasks; and
   means for storing the at least one downlinked RAM-based task and the at least one RAM-based task pointer in an electrically erasable programmable read only memory ("EEPROM").

2. The system as in claim 1 further comprising means for storing the downlinked code and pointers in an electrically erasable programmable read only memory ("EEPROM") before the downlinked code and pointers are stored in the RAM.

3. The system as in claim 1 further comprising means for restoring the at least one downlinked RAM-based task and the at least one downlinked RAM-based task pointer to RAM from the EEPROM upon detecting a RAM fault.

4. The system as in claim 3 further comprising means for terminating execution of at least one RAM-based task upon failure of the means for restoring the downlinked code and pointers from EEPROM to cure the RAM failure.

5. The system as in claim 4 further comprising means for reverting back to execution of at least one ROM-based task corresponding to the at least one RAM-based task for which execution was terminated.

6. A hybrid random access memory ("RAM") and read only memory ("ROM") system for use in a medical treatment device that is implantable within the body of a patient, the system comprising:
   a ROM containing
     a function defaults module for storing functions in the ROM,
     a function pointer defaults module for storing pointers to the functions stored in the function defaults module of the ROM,
     an executive/task scheduler for executing functions pointed to by stored function pointers, and
     a task order defaults module for defining the initial order in which ROM-based tasks are executed;
   a RAM containing
     a function pointer table for storing pointers to the functions executed by the executive/task scheduler, the function pointer table being initialized by copying the contents of the function pointer defaults module from the ROM and,
     a downlinked functions module for storing downlinked functions, and
     a task order table for storing downlinked definitions of the order in which ROM-based tasks or RAM-based tasks, or both ROM-based tasks and RAM-based tasks are executed, the task order table being initialized by copying the contents of the task order defaults module of the ROM; and
   a programmer and telemetry link for downlinking the functions stored in the downlinked functions module of the RAM.

7. The system as in claim 6, further comprising: an electrically erasable programmable read only memory containing:
   a function pointer changes module for storing a back-up copy of the contents of the function table pointer of the RAM, a function changes module for storing a back-up copy of the downlinked functions module of the RAM, and a task order changes module for storing a back-up copy of the task order table of the RAM.

8. The system as in claim 7 further comprising means for restoring the contents of at least one module of the RAM, upon a RAM failure, by copying the contents of the corresponding back-up module from the EEPROM.

9. The system as in claim 8, further comprising means for terminating execution of at least one RAM-based function upon failure of copying the contents of the corresponding back-up module from EEPROM to cure the RAM failure.

10. The system as in claim 9, further comprising means for executing at least one ROM-based function corresponding to the at least one terminated RAM-based function.

11. A method of storing control software in a human-implantable medical treatment device comprising the steps of:

storing in a read only memory ("ROM") a task scheduler and a plurality of ROM-based tasks to be performed by the medical treatment device;

storing in a random access memory ("RAM") a plurality of ROM-based task pointers pointing to the ROM-based tasks;

downlinking to the RAM at least one RAM-based task thereby producing at least one downlinked RAM-based task;

downlinking to the RAM at least one RAM-based task pointer thereby producing at least one downlinked RAM-based task pointer pointing to at least one of the at least one downlinked RAM-based tasks such that the medical treatment device uses at least one of the ROM-based task pointer to execute at least one of the ROM-based tasks and uses at least one of the downlinked RAM-based task pointers to execute at least one of the downlinked RAM-based tasks; and storing the at least one downlinked RAM-based task and the at least one downlinked RAM-based task pointer in an electrically erasable programmable read only memory ("EEPROM").

12. The method as in claim 11 further comprising the step of storing the downlinked code and pointers in an electrically erasable programmable read only memory ("EEPROM") before the downlinked code and pointers are stored in the RAM.

13. The method as in claim 11 further comprising the step of restoring the at least one downlinked RAM-based task and the at least one downlinked RAM-based task pointer to RAM from the EEPROM upon detecting a RAM fault.

14. The system as in claim 13 further comprising the step of terminating execution of at least one RAM-based task upon failure of restoring the downlinked code and pointers from EEPROM to cure the RAM failure.

15. The method as in claim 14 further comprising the step of reverting back to execution of at least one ROM-based task corresponding to the at least one RAM-based task for which execution was terminated.

* * * * *